United States Patent
Ho et al.

(10) Patent No.: US 8,365,958 B2
(45) Date of Patent: Feb. 5, 2013

(54) DEVICE FOR MIXING AND DISCHARGING PLURAL MATERIALS

(75) Inventors: Phillip Phung-I Ho, Santa Barbara, CA (US); Chung-Chieh Lee, Taipei Hsien (TW)

(73) Assignee: Phillip Phung-I Ho, Santa Barbara, CA (US)

( * ) Notice: Subject to any disclaimer, the term of this patent is extended or adjusted under 35 U.S.C. 154(b) by 415 days.

(21) Appl. No.: 12/704,888

(22) Filed: Feb. 12, 2010

(65) Prior Publication Data

US 2011/0198370 A1 Aug. 18, 2011

(51) Int. Cl.
*B67D 7/70* (2010.01)
*B67D 7/78* (2010.01)

(52) U.S. Cl. ............... 222/137; 222/142; 222/145.1; 222/145.5; 222/145.6

(58) Field of Classification Search ............ 222/137, 222/142, 145.1, 145.5, 145.6; 604/416
See application file for complete search history.

(56) References Cited

U.S. PATENT DOCUMENTS

| | | | |
|---|---|---|---|
| 4,432,469 A | 2/1984 | Eble et al. | |
| 4,989,758 A * | 2/1991 | Keller | 222/137 |
| 5,033,650 A * | 7/1991 | Colin et al. | 222/137 |
| 5,443,183 A * | 8/1995 | Jacobsen et al. | 222/145.6 |
| 6,547,101 B1 | 4/2003 | Sogaro | |
| 6,698,622 B2 * | 3/2004 | Sawhney et al. | 222/137 |
| 6,843,652 B2 * | 1/2005 | Xie et al. | 433/90 |
| 7,938,296 B2 * | 5/2011 | Keller | 222/145.5 |
| 8,033,429 B2 * | 10/2011 | Keller | 222/145.6 |
| 2008/0128454 A1 * | 6/2008 | Beckett | 222/137 |
| 2009/0152300 A1 * | 6/2009 | Hayman et al. | 222/145.6 |

* cited by examiner

*Primary Examiner* — Kevin P Shaver
*Assistant Examiner* — Nicolas Weiss
(74) *Attorney, Agent, or Firm* — WPAT, P.C.; Anthony King

(57) ABSTRACT

A device for mixing and discharging plural materials has a body, a housing and a sealing plug. The body has multiple barrels and multiple tubes communicating with the barrels. The housing is rotatably attached to the body in a thread manner and has a mixing chamber and a discharging segment. The sealing plug is mounted in the mixing chamber to seal the tubes and has a sealing disk and multiple sealing sleeves. The sealing disk has multiple holes and multiple sealing lids mounted respectively in the holes, and each sealing lid has an outer edge connected detachably to the inner surface of a corresponding hole and having a thickness smaller than that of the sealing lid. The sealing sleeves are formed on the sealing disk, align respectively with the holes in the sealing disk and are mounted respectively around the tubes.

14 Claims, 6 Drawing Sheets

DEVICE FOR MIXING AND DISCHARGING PLURAL MATERIALS

BACKGROUND OF THE INVENTION

1. Field of the Invention

The present invention relates to a device, and more particularly to a device for mixing and discharging plural materials.

2. Description of Related Art

A device for mixing multiple materials, such as an ampoule is widely used in medicine, cosmetics or other fields.

U.S. Pat. No. 6,547,101, entitled to "Multi-Chambered Ampoule For Dispensing A Mixture Comprising Several Substances" disclosed an ampoule comprising an oblong container, a sealing means, a housing and at least two pistons. The oblong container has at least two substance chambers, and the sealing means is for sealing the substance chambers at an end of the container. After the sealing effect provided by the sealing means being removed, the substances in the chamber can be mixed and dispensed from the housing. The '101 patent disclosed multiple embodiments for the sealing means, such as a foil with a pull-off section and a sealing plug with two legs and a membrane. However, to pull the foil out of the housing is troublesome plus the sealing plug cannot provide a sufficient sealing effect, and the membrane may not break.

U.S. Pat. No. 4,432,469, entitled to "Device For Discharging A Plural-Component Material" disclosed a device for discharging measured amounts of a plural-component material and comprising a casing and a rotatable member. However, the structure and operation of the device of "469 patent is complex.

U.S. Pat. No. 3,687,982, entitled to "Adhesive And Sealant Dispenser With Grinding means" disclosed a mixing and dispensing unit for accommodating several materials. However, the dispenser of the '982 patent does not provide a sealing effect to the cylinder, so the dispenser cannot be used to house materials whose components, as well as their vapors, need to be kept separated before use.

To overcome the shortcomings, the present invention tends to provide a device for mixing and discharging plural materials to mitigate or obviate the aforementioned problems.

SUMMARY OF THE INVENTION

The main objective of the invention is to provide a device for mixing and discharging plural materials. The device has a body, a housing and a sealing plug. The body has a front end, a rear end, a front board, multiple barrels and multiple tubes. The front board is formed at the front end and has a front side and a rear side. The barrels are formed on and protrude from the rear side of the front board and extend toward the rear end of the body. The tubes are formed on and protrude from the front side of the front board and communicate respectively with the barrels. Each tube has a free end provided with an opening. The housing is rotatably attached to the front end of the body in a thread manner and has a front end, a rear end a rear end connected to the front end of the body, a mixing chamber and a discharging segment. The mixing chamber is defined in the rear end of the housing and is mounted around and communicates with the openings of the tubes on the body. The discharging segment is formed on, protrudes from and communicates with the mixing chamber. The sealing plug is mounted in the mixing chamber, is attached to the front end of the body to seal the tubes and has a sealing disk and multiple sealing sleeves. The sealing disk is attached to and seals the openings of the tubes on the body and has multiple holes and multiple sealing lids. The holes are defined through the sealing disk and align respectively with the tubes on the body. The sealing lids are mounted respectively in and seal the holes, and each sealing lid has an outer edge connected detachably to the inner surface of the corresponding holes and having a thickness smaller than that of the sealing lid. The sealing sleeves are formed on and protrude from the sealing disk, align respectively with the holes in the sealing disk and are mounted respectively around the tubes on the body.

Other objects, advantages and novel features of the invention will become more apparent from the following detailed description when taken in conjunction with the accompanying drawings.

DETAILED DESCRIPTION OF PREFERRED EMBODIMENT

Figure 1:
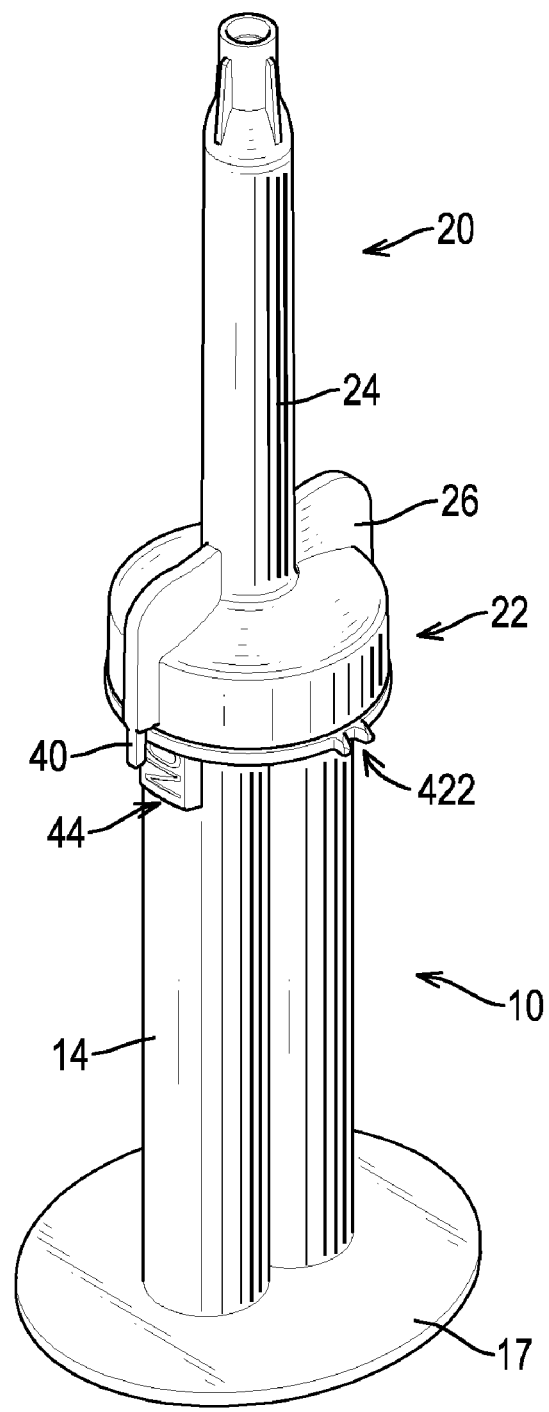
FIG. 1 is a perspective view of a device for mixing and discharging plural materials in accordance with the present invention.
Figure 2:
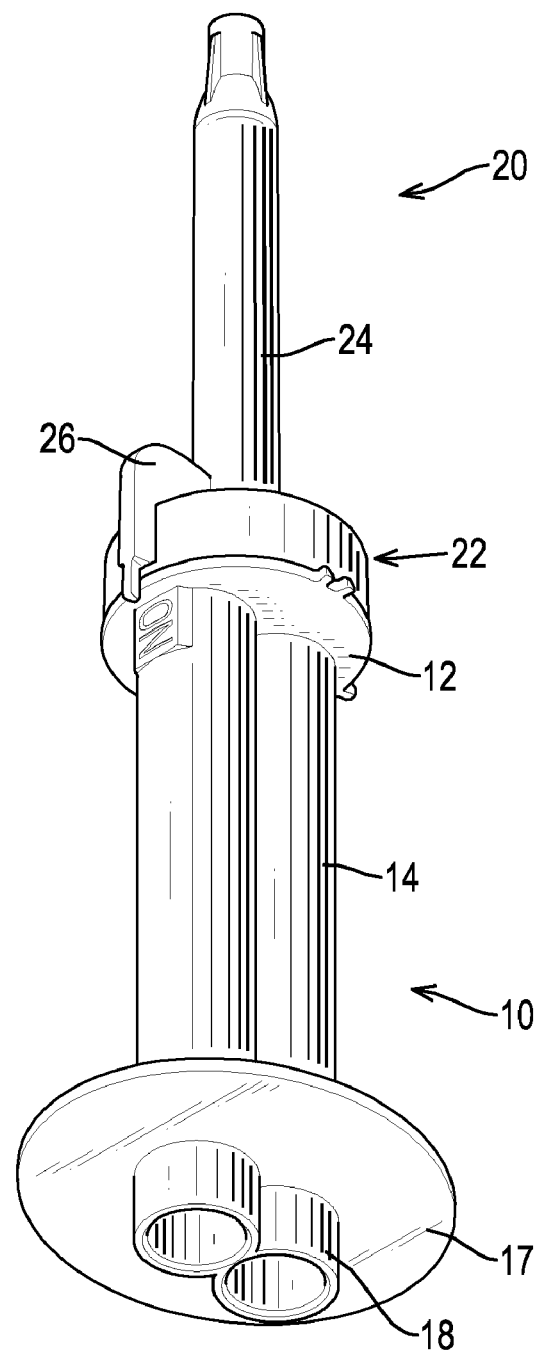
FIG. 2 is another perspective view of the device in FIG. 1
Figure 3:
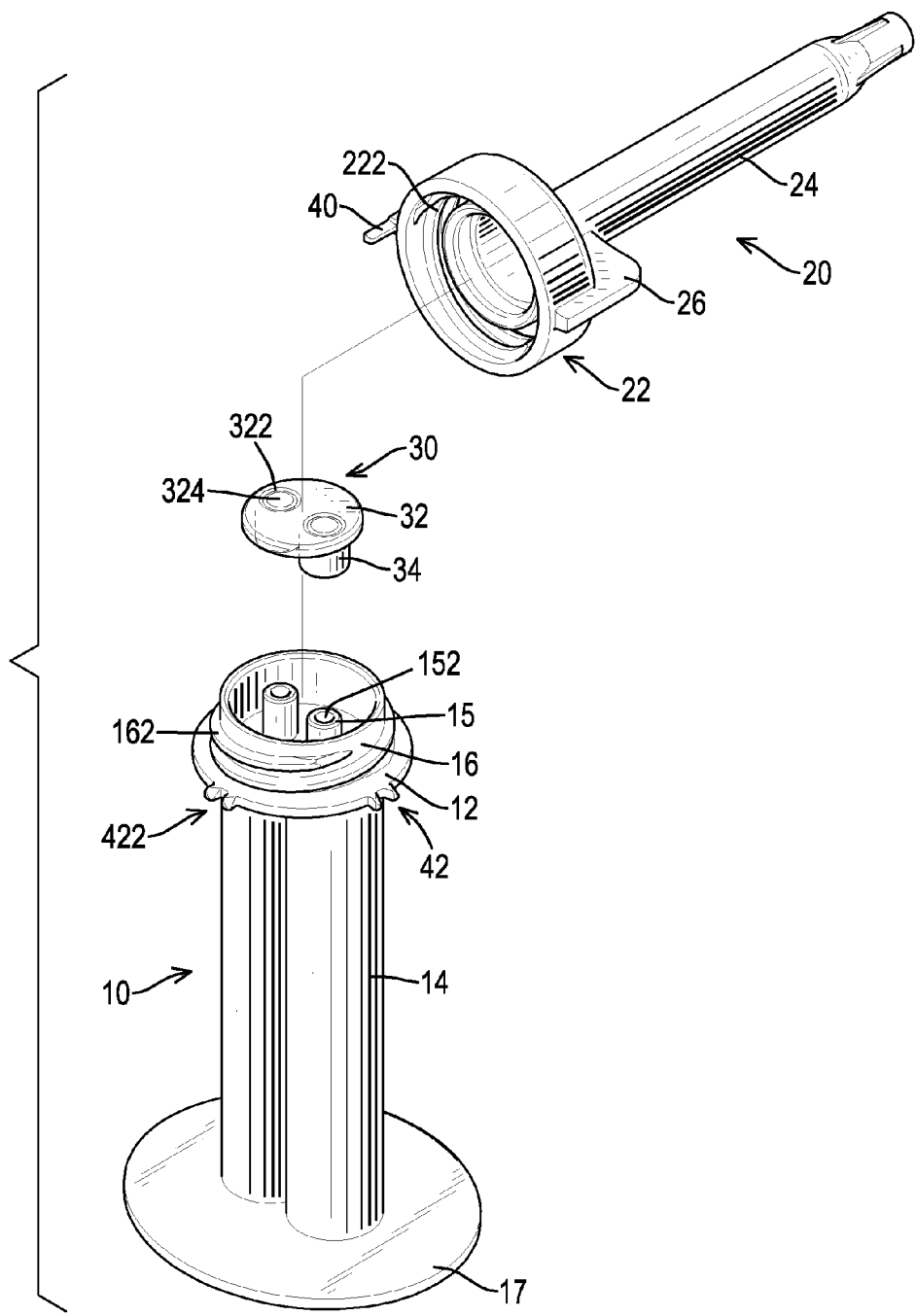
FIG. 3 is an exploded perspective view of the device in FIG. 1.

With reference to FIGS. 1 to 4, a device for mixing and discharging plural materials in accordance with the present invention comprises a body (10), a housing (20), a sealing plug (30) and a positioning device. The body (10) has a front end, a rear end, a front board (12), multiple barrels (14), multiple tubes (15), an annular combing wall (16), a finger flange (17) and multiple sockets (18).

The front board (12) is formed at the front end and has a front side and a rear side. The barrels (14) are formed on and protrude from the rear side of the front board (12) and extend toward the rear end of the body (10). The tubes (15) are formed on and protrude from the front side of the front board (12) and communicate respectively with the barrels (14) via passages defined through the front board (12). Each tube (15) has an opening (152) defined in the free end of the tube (15). Preferably, two barrels (14) and two tubes (15) are implemented. The annular combing wall (16) is formed on the front end around the tubes (15) and has an outer thread (162) formed around the combing wall (16). The finger flange (17) is formed around the rear end of the body (10). The sockets (18) are formed on and protrude from the finger flange (17) and respectively align and communicate with the barrels (14) via passages defined through the finger flange (17). In the preferred embodiment, two sockets (18) are implemented.

The housing (20) is rotatably attached to the front end of the body (10) in a thread manner and comprises a front end, a rear end, a mixing chamber (22), a discharging segment (24) and multiple reinforced ribs (26). The rear end of the housing (20) is connected to the front end of the body (10). The mixing chamber (22) is defined in the rear end of the housing (20) and is mounted around and communicates with the openings (152) of the tubes (15) on the body (10). The mixing chamber (22) has an inner thread (222) formed in the inner surface of the mixing chamber (22) and screwed with the outer thread (162) on the combing wall (16) of the body (10) to rotatably combine the housing (20) with the body (10) in a thread manner. The discharging segment (24) is tubular and is formed on, protrudes from and communicates with the mixing chamber (22). The reinforced ribs (26) are formed on the outer surface of the mixing chamber (22).

The sealing plug (30) is mounted in the mixing chamber (22), is attached to the front end of the body (10) to seal the openings (152) of the tubes (15) and comprises a sealing disk (32) and multiple sealing sleeves (34). The sealing disk (32) is attached to and seals the opening (152) of the tubes (15) on the body (10) and has multiple holes (322) and multiple sealing lids (324). The holes (322) are defined through the sealing disk (32) and aligning respectively with the tubes (15) on the body (10). The sealing lids (324) are mounted respectively in and sealing the holes (322), and each sealing lid (324) having an outer edge connected detachably to an inner surface of a corresponding one of the holes (322) and having a thickness smaller than that of the sealing lid (324). The sealing sleeves (34) are formed on and protrude from the sealing disk (32), align respectively with the holes (322) in the sealing disk (32) and are mounted respectively around the tubes (15) on the body (10).

The positioning device is mounted between the body (10) and the housing (20) and comprises a positioning tab (40), multiple notches (42,422) and a mark (44). The positioning tab (40) is formed on the housing (20), may be formed on one of the reinforced ribs (26) and protrudes toward the body (10). The notches (42,422) are formed separately in the outer periphery of the front board (12) of the body (10) and selectively engage the positioning tab (40) on the housing (20). Preferably, two notches (42,422) are implemented, and the notches (42,422) are separated from each other at an interval of 90° in radian. The mark (44) is formed on one of the barrels (14) is separated from one of the notches at an interval of 90° in radian.

Figure 4:
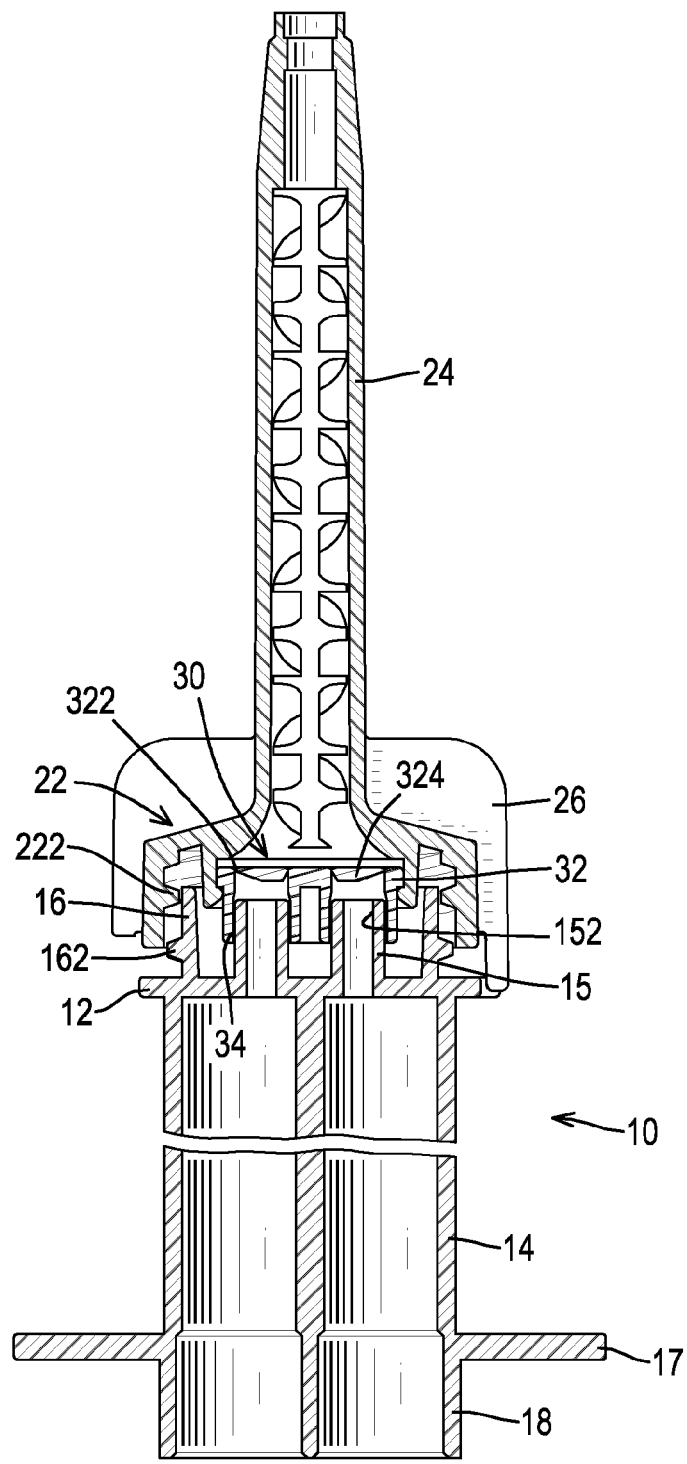
FIG. 4 is an enlarged cross sectional side view of the device in FIG. 1 in an original condition.

With reference to FIG. 4, at an original condition, the housing (20) is at a position where the sealing disk (32) is spaced from the openings (152) of tubes (15) on the body (10) and the positioning tab (40) engages a first notch (42) in the front board (12).

Figure 5:
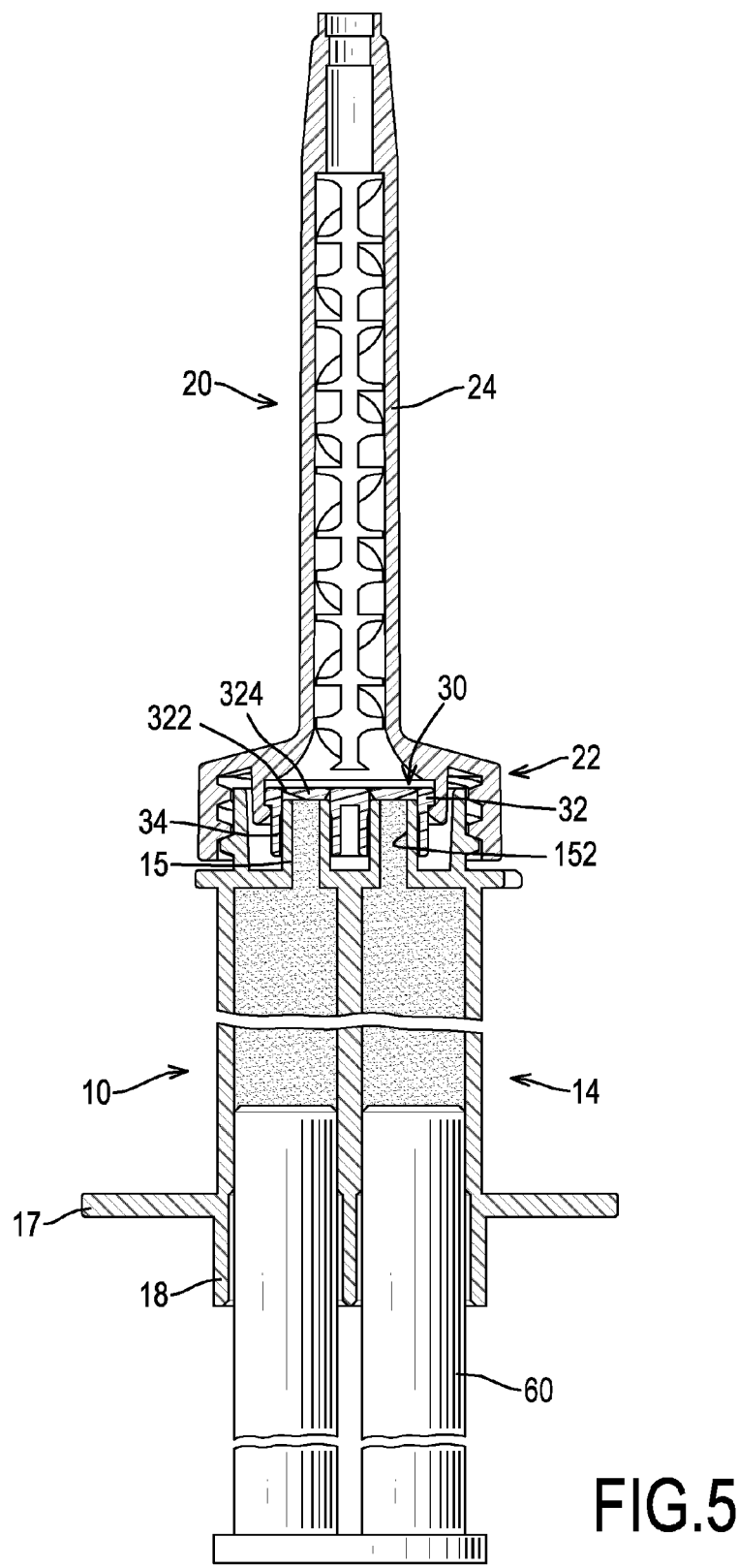
FIG. 5 is an enlarged cross sectional side view of the device in FIG. 1 in a material-filled condition.

With reference to FIGS. 1 and 5, after materials, such as medicaments, cosmetic substances or the like being fed into the barrels (14) via the sockets (18), the housing (20) is rotated in 90° relative to and moved toward the body (10) to make the tubes (15) abutting with and being sealed by the corresponding sealing lids (324). A plunger (60) with multiple pistons is inserted into the barrels (14) via the sockets (18). Consequently, the sealing plug (30) seals the tubes (15) and the barrels (14) to hold the materials in the barrels (14). At this time, the positioning tab (40) engages a second notch (422) in the body (10).

Figure 6:
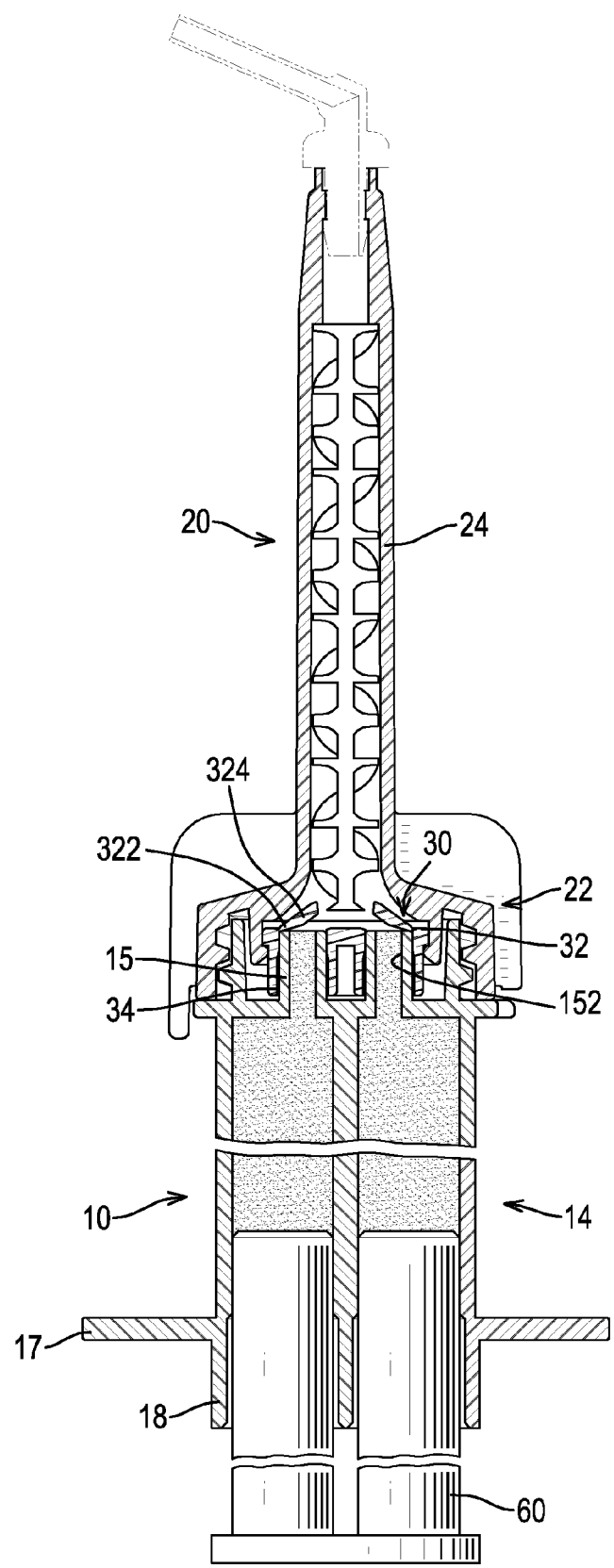
FIG. 6 is an enlarged cross sectional side view of the device in FIG. 1 in a discharging condition.

With reference to FIGS. 1 and 6, when the user wants to mix and discharge the materials, the housing (20) is further rotated in 90° to make the housing (20) move further toward the body (10). With the movement of the housing (20), the tubes (15) push against the sealing lids (324) and the sealing lids (324) will be separated from the holes (322). Consequently, the tubes (15) are communicated with the mixing chamber (22) to allow the materials being fed into and mixed in the mixing chamber (22) and being discharged from the discharging segment (24) by pushing the plunger (60).

With such an arrangement, the materials held in the barrels (14) can be actually sealed by the sealing plug (30), so the materials can be effectively prevented from accidental mixing even after the materials are held in the barrels (14) a long time. Additionally, the positioning device can provide a positioning effect to hold the housing (20) at different operating conditions relative to the user, so the operation of the device in accordance with the present invention is convenient.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A device for mixing and discharging plural materials comprising:
   a body having
      a front end;
      a rear end;
      a front board formed at the front end and having a front side and a rear side;
      multiple barrels formed on and protruding from the rear side of the front board and extending toward the rear end of the body; and
      multiple tubes formed on and protruding from the front side of the front board and communicating respectively with the barrels, and each tube having a free end provided with an opening;
   a housing rotatably attached to the front end of the body in a thread manner and comprising
      a front end;
      a rear end connected to the front end of the body;
      a mixing chamber defined in the rear end of the housing and mounted around and communicating with the openings of the tubes on the body; and
      a discharging segment formed on, protruding from and communicating with the mixing chamber; and
   a sealing plug mounted in the mixing chamber, attached to the front end of the body to seal the tubes and comprising
      a sealing disk attached to and selectively sealing the openings of the tubes on the body and having
         multiple holes defined through the sealing disk and aligning respectively with the tubes on the body; and
         multiple sealing lids mounted respectively in and selectively sealing the holes, and each sealing lid having an outer edge connected detachably to an inner surface of a corresponding one of the holes and having a thickness smaller than that of the sealing lid; and
      multiple sealing sleeves formed on and protruding from the sealing disk, aligning respectively with the holes in the sealing disk and mounted respectively around the tubes on the body, wherein
   at an original condition, the sealing disk is spaced from the openings of the tubes on the body.

2. The device as claimed in claim 1, wherein
   the body further has an annular combing wall formed on the front end around the tubes of the body and having an outer thread formed around the combing wall; and
   the housing further has an inner thread formed in an inner surface of the mixing chamber and screwed with the outer thread on the combing wall of the body.

3. The device as claimed in claim 2, wherein the body further has
   a finger flange formed around the rear end of the body; and
   multiple sockets formed on and protruding from the finger flange and respectively aligning and communicating with the barrels.

4. The device as claimed in claim 3 further comprising a positioning device mounted between the body and the housing and comprising
- a positioning tab formed on the housing and protruding toward the body; and
- multiple notches formed separately in an outer periphery of the front board of the body and selectively engaging the positioning tab on the housing.

5. The device as claimed in claim 4, wherein the positioning device has two notches and further has a mark formed on one of the barrels, wherein
- the notches are separated from each other at an interval of 90° in radian; and
- the mark is separated from one of the notches at an interval of 90° in radian.

6. The device as claimed in claim 5, wherein the housing further has multiple reinforced ribs formed on an outer surface of the mixing chamber, and the positioning tab is formed on one of the reinforced ribs.

7. The device as claimed in claim 6, wherein the body has two barrels, two tubes and two sockets; and
- the sealing plug has two sealing sleeves and two sealing lids.

8. The device as claimed in claim 1, wherein the body further has
- a finger flange formed around the rear end of the body; and
- multiple sockets formed on and protruding from the finger flange and respectively aligning and communicating with the barrels.

9. The device as claimed in claim 1 further comprising a positioning device mounted between the body and the housing and comprising
- a positioning tab formed on the housing and protruding toward the body; and
- multiple notches formed separately in an outer periphery of the front board of the body and selectively engaging the positioning tab on the housing.

10. The device as claimed in claim 9, wherein the positioning device has two notches and further has a mark formed on one of the barrels, wherein
- the notches are separated from each other at an interval of 90° in radian; and
- the mark is separated from one of the notches at an interval of 90° in radian.

11. The device as claimed in claim 10, wherein the housing further has multiple reinforced ribs formed on an outer surface of the mixing chamber, and the positioning tab is formed on one of the reinforced ribs.

12. The device as claimed in claim 11, wherein the body has two barrels, two tubes and two sockets; and
- the sealing plug has two sealing sleeves and two sealing lids.

13. The device as claimed in claim 1, wherein the housing further has multiple reinforced ribs formed on an outer surface of the mixing chamber.

14. The device as claimed in claim 1, wherein the body has two barrels and two tubes; and
- the sealing plug has two sealing sleeves and two sealing lids.

* * * * *